(12) United States Patent
Utterberg et al.

(10) Patent No.: US 7,591,804 B2
(45) Date of Patent: Sep. 22, 2009

(54) SHORT WINGED NEEDLE AND GUARD

(75) Inventors: David S. Utterberg, Seattle, WA (US); William J. Schnell, Libertyville, IL (US); David Bell, Grayslake, IL (US)

(73) Assignee: DSU Medical Corporation, Las Vegas, NV (US)

( * ) Notice: Subject to any disclaimer, the term of this patent is extended or adjusted under 35 U.S.C. 154(b) by 244 days.

(21) Appl. No.: 11/407,716

(22) Filed: Apr. 20, 2006

(65) Prior Publication Data

US 2007/0250014 A1 Oct. 25, 2007

(51) Int. Cl.
*A61M 5/32* (2006.01)
(52) U.S. Cl. .................... 604/177; 604/192; 604/162; 604/164.08
(58) Field of Classification Search .......... 604/272, 604/177, 192, 197, 162, 263, 164.08, 198
See application file for complete search history.

(56) References Cited

U.S. PATENT DOCUMENTS

| | | | |
|---|---|---|---|
| 4,820,282 A * | 4/1989 | Hogan | ............... 604/263 |
| 4,935,011 A | 6/1990 | Hogan | |
| 5,030,212 A | 7/1991 | Rose | |
| 5,433,703 A | 7/1995 | Utterberg et al. | |
| 5,562,637 A * | 10/1996 | Utterberg | ............... 604/263 |
| 5,951,529 A | 9/1999 | Utterberg | |
| 5,983,947 A | 11/1999 | Utterberg | |
| 6,616,635 B1 * | 9/2003 | Bell et al. | ............... 604/192 |
| 2004/0102739 A1 | 5/2004 | Nakajima | |

FOREIGN PATENT DOCUMENTS

| | | |
|---|---|---|
| WO | WO 01/74416 A2 | 3/2001 |
| WO | WO 0230491 | 4/2002 |

* cited by examiner

*Primary Examiner*—Kevin C Sirmons
*Assistant Examiner*—Deanna K Hall
(74) *Attorney, Agent, or Firm*—Seyfrath Shaw LLP (57) ABSTRACT

A winged needle comprises a hollow medical needle which typically is no smaller than 18 gauge carried by a hub. The hub has wings projecting laterally outwardly, the wings having outer tips that are spaced from each other by essentially 20 to 30 mm. A guard for a winged needle tube set is also disclosed, in which the guard comprises a needle guard tube free of wing-receiving slots and defining a forward, open end to receive a winged needle having outwardly extending, substantially unbent wings as positioned within the guard. In some embodiments, the guard comprises a substantially fixed, open mouth having a width of at least 20 mm and a height of at least 5 mm. A novel anchor strip having two flex lines is also provided to the guard.

25 Claims, 5 Drawing Sheets

SHORT WINGED NEEDLE AND GUARD

BACKGROUND OF THE INVENTION

The currently available winged needle sets and prior art, particularly those using relatively large diameter needles typically larger than about 17 gauge, have "wings" that are believed to be at least 34 mm. wide on arteriovenous fistula sets. This is true when the tubing of said sets is large, typically with an outer diameter of at least about 5.0 mm., and when small tubing on scalp vein sets has only an outer diameter of 2 mm. or less.

It is now mandated by law that many needle sets must carry a needle protector to protect handlers of the set from accidental needle stick, after the needle has been used and withdrawn from the patient. An example of such a device is the Master-Guard® Slotted Needle Guard sold by Medisystems Corporation of Seattle, Wash., in which the needle guard passes along the wings of the needle to be protected, with the wings projecting outwardly through the slots.

Various slotless tubular needle guards are known as well, one such guard being proposed for use with a winged needle, namely the WingEater needle guard of JMS Co., Ltd., as illustrated in PCT published application WO 02/30491 A1 (in Japanese). A problem with this design resides in the difficulty in getting the wings to fold properly as a wide mouthed tube is advanced to enclose the winged needle by the tubular needle guard. Furthermore, the WingEater needle guard has a small pocket at the bottom of the front end thereof for capturing the point of the needle. In the practice of hemodialysis, the needle is often "flipped" by 180° rotation after insertion into the vein, in an attempt to maximize blood flow through the needle. In the flipped position, it is difficult or impossible for the needle tip, when removed from the patient, to be captured by the forward pocket of the WingEater device.

In accordance with this invention, a realization has arisen that there is no real need, especially in the case of larger winged needle sets where the needles are essentially no smaller than about 17 gauge, for the wings to be as wide as 34 mm. or more. Such hubs are large enough to be more readily graspable on their own than hubs of smaller needles. It may be that aesthetics has been a chief driving force for the design, but, in fact, it has been determined in accordance with this invention that a substantially narrower wing is useable, even with the larger diameter needles utilized in hemodialysis, blood collection, and the like. With a narrower wing, it becomes possible to develop a tubular, open-ended needle guard which can receive a winged needle without any need to fold the wings. Such a needle guard may have the advantage of easy needle insertion, plus a sealing capability against spillage of blood from the tubular needle set which carries the guard while the needle is guarded. By this invention, a set can be completely sealed after use. Also, the set can be safely and effectively sealed whether the winged needle is in the normal or the "flipped" position.

DESCRIPTION OF THE INVENTION

In accordance with this invention, a winged needle comprises a hollow medical needle which typically is essentially no smaller than 17 gauge. The needle is carried by a hub, the hub also carrying wings which project laterally outwardly from the hub in opposed directions. The wings have outer tips that are spaced from each other by essentially 20 to 30 mm., rather than the prior art outer wing tip spacing of at least about 34 mm. for larger needles of 17 gauge and more. Preferably, the outer tips may be spaced by no more than essentially 27 mm.

As is conventional, the needle and hub are connected to flexible tubing, to comprise an arteriovenous fistula set or other set, particularly a set that is intended for access to blood.

A tubular, slot-free, hollow needle guard, having self-supporting walls to define an inner chamber, may be carried on the tubing, with the needle guard defining a forward, end opening having a generally stable, two dimensional cross-sectional area. The hollow guard is proportioned to receive and surround the winged needle without substantial bending of the wings, which renders such a needle guard easier to install around the winged needle of this invention, when compared with other known, slotless needle guards. To accomplish this, the open end of the needle guard and the inner chamber, typically define an aperture having a horizontal dimension of essentially 20 mm. or greater, and a vertical dimension of essentially 3 mm. or more, sufficient to accomplish easy entry of the winged needle without substantial bending of the wings. This self-supporting, chamber-defining shape for a needle guard is different from, and advantageous over, the flexible envelope-type needle guards of Hogan U.S. Pat. Nos. 4,935,011 and 4,820,282, being substantially rigid in some embodiments, with the end opening having a substantially fixed dimension, but being typically subject to the slight resilience found in most hollow plastic items.

Furthermore, by this invention a similar guard for a winged tube set is provided having a hollow needle, a needle hub, and flexible set tubing attached to the hub. The guard comprises a needle guard tube which is free of wing-receiving slots, and defining a forward, open end. When in use, the guard tube contains a winged needle of a set, which winged needle has outwardly extending, substantially unbent wings positioned within the guard. The guard comprises a fixed-dimension, open mouth having a width of at least about 20 mm, a height of at least about 5 mm., and preferably a mouth having a width of essentially at least 25 mm., and generally no more than essentially 35 mm. Such a guard is generally utilized with a winged needle which can be received within the guard without substantial bending of the wings out of their initial, generally planar shape.

Further in accordance with this invention, a guard for a winged needle tube set of the above type having a hollow needle, a needle hub, and flexible set tubing attached to the hub may comprise a needle guard tube which is free of wing-receiving slots and which defines a forward, open end. An anchor strip may be attached to the forward end. The anchor strip may be attached to the rest of the guard by a first flex line, permitting transverse rotational movement of the anchor strip relative to the guard tube. This transverse, rotational movement may be either vertical, horizontal, or in some diagonal direction, and the first flex line may be carried on the anchor strip adjacent to the rest of the needle guard tube. A second flex line may also be defined in the anchor strip, spaced from and preferably parallel to the first flex line, permitting free, added rotational movement of an outer portion of the anchor strip.

Preferably, the first flex line is connected to a top wall of a generally rigid needle guard tube, and is substantially horizontal, to permit substantially vertical transverse rotational movement of essentially the entire anchor strip. The needle guard tube may be of rectangular cross section.

In some embodiments, the forward, open end of the needle guard tube may be partially defined by a bottom wall of the needle guard, which bottom wall extends horizontally beyond the top wall of the needle guard. The first and second flex lines may be spaced apart at about the distance of the height of the open end, to permit the anchor strip to pivot to close the open end, in which closed position the anchor strip occupies an L-shaped configuration, with an outer portion of the anchor strip lying against the bottom wall. It will also be seen in the drawings that outermost portions of the anchor strip may be spaced from the bottom wall.

In some embodiments, the anchor strip described above may define an outwardly extending projection between the first and second flex lines. This projection may be used to assist in the manual closing of the open end of the guard tube, to press the anchor strip into its L-shaped configuration, and to thus close and preferably seal the open end of the guard tube.

In some embodiments, the guard of this invention may carry a flow-blocking, tapered projection which is proportioned to sealingly engage a female luer. Such a female luer is typically carried by the winged needle tube set which carries the guard of this invention.

It also may be desirable for various embodiments of the guard of this invention to carry internal tube centering ribs.

In some embodiments, the needle guard of this invention defines a rear aperture through which the flexible tubing extends, with the hub being connected with the flexible tubing, where a first portion of the tubing is positioned outside and around a portion of the hub, and this first portion defines an increased outer diameter, when compared with the remaining portions of the flexible tubing. This may be accomplished by providing a first portion of the flexible tubing which is naturally of slightly larger outer diameter, or the flexible tubing used may be all naturally of the same outer diameter, but the first portion is stretched by being placed on a projecting rigid or semi-rigid tube of the hub, which stretches that first portion of the flexible tubing into an outer diameter which is greater than the natural outer diameter of the rest of the flexible tubing.

In accordance with this invention, the rear aperture is sized to permit easy sliding of the remaining portions of the flexible tubing through it, so that the guard of this invention may easily slide along the flexible tubing, being captured and held on the flexible tubing by the fact that the flexible tubing passes through the rear aperture of the guard. However, edges of the rear aperture bind against the first portion of the tubing, since it is of larger outer diameter, to form a seal with the first tubing portion, when the first portion extends through the rear aperture of the guard. The increase in outer diameter of the first tubing portion only has to be a few thousands of an inch for the guard to slide easily along most of the tubing, but to bind against and form a seal with the first portion of the tubing carried on the hub, so that blood which leaks from the needle into the interior of the guard does not leak out of the rear aperture when the needle is enclosed in the guard.

The needle of a needle tube set may be safely removed from a first position in which the needle penetrates a patient, to a second position where the needle is safely enclosed in a needle guard tube, by a method which comprises:

advancing the needle guard tube having an open front end, while threaded on the tube set, into adjacent relation with the needle in the first position;

pressing against the patient an anchor strip attached to the needle guard tube as said strip extends forwardly over the needle, while pulling the needle tube set to retract the needle from the patient, and to cause the needle to fully enter the needle guard tube;

bending the anchor strip along a first flex line across the open end of the needle guard tube; and bending an outer portion of the anchor strip along a second flex line to cause the anchor strip to assume an L-shape, and wedging said anchor strip into closing relation with the open end.

The open, front end of the guard may be partially defined by a bottom wall of the needle guard tube which extends horizontally beyond the top wall of the needle guard tube. An outer portion of the anchor strip lies against the bottom wall when in L-shape and is wedged into closing relation with the open end.

Thus, a guard is provided which can seal its front end after the winged needle is enclosed, while preferably avoiding the difficulties which can arise with a guard which bends and folds the flexible needle wings as the needle is drawn into the guard. Because of the lateral forces created by such wing folding, the needle tip can thrash side to side or up and down during its removal from a blood vessel, doing significant damage to the blood vessel and resulting in a possible hematoma.

Furthermore, the use of needles with a shortened wing width enables the needle to be "flipped" (rotated by 180°) more safely than with longer wings, as the physician or nurse seeks better blood flow from the fistula or vein which has been penetrated. Up until now, special, more costly "rotatable hub" sets were needed to flip needles easily and safely. However, a short, fixed wing as described herein flips with the essential ease of a rotatable wing, but does not exhibit the problems with such rotatable hubs, namely difficulty in control of the needle point bevel and point position of the needle both before, during, and after cannulation.

As a further advantage, a typical, known taping scheme for safely securing a winged needle to the skin of a patient has been the so called "chevron design". A tape loop is placed under the tube of the winged needle set, and then the lengths of tape from the loop are crossed over each wing. This is a fairly difficult manual process, which requires manipulation of the needle hub and wings in a way that can cause movement of the sharp needle tip in the blood vessel, thus risking hematomas. A shorter, fixed wing set requires much less manipulation to install taping in the conventional Chevron pattern.

Furthermore, the winged needle can advance into the guard of this invention with resistance forces that are substantially less than guards where the wing must be folded. For example, while the WingEater guard generally requires an entry force of about 550 grams to fold the wings and cause entry of the needle into the guard, the guard of this invention, engaging a winged needle as described herein, may enter its guard at a force of about 210 grams or less, since the wing is not being folded or otherwise significantly bent.

DESCRIPTION OF SPECIFIC EMBODIMENTS

Figure 1:
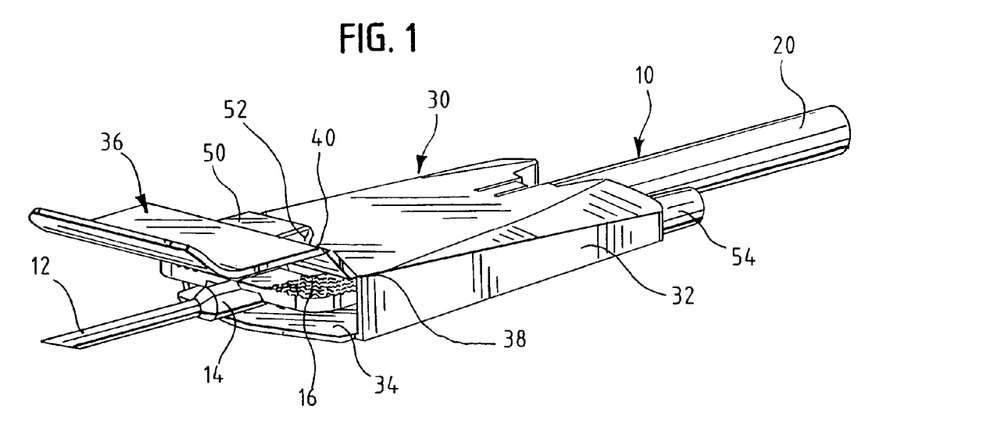
FIG. 1 is a perspective view of a winged needle and hub, entering into an open-mouthed guard in accordance with this invention.
Figure 2:
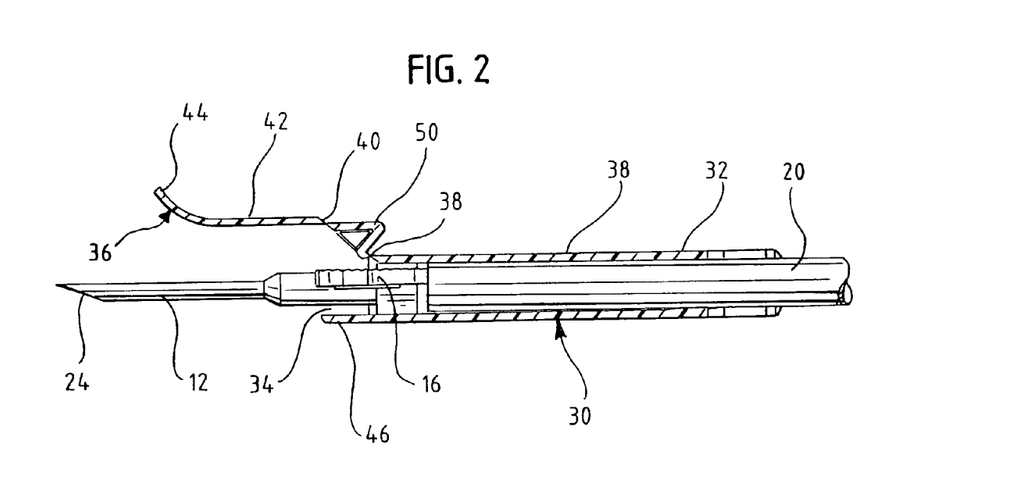
FIG. 2 is an elevational view of the needle and hub, and a longitudinal sectional view of the guard, of FIG. 1.
Figure 3:
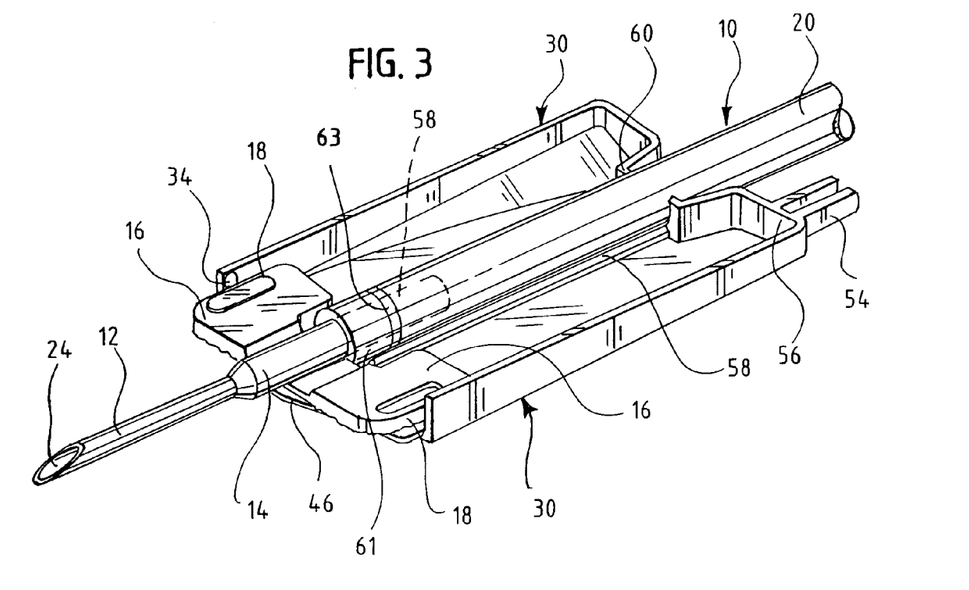
FIG. 3 is an enlarged, perspective view of the needle set and guard of FIG. 1, with the upper portion of the guard broken away for interior viewing.

Referring to the drawings, and particularly FIGS. 1-3, a winged needle set is disclosed, particularly an arteriovenous fistula set for hemodialysis, comprising a hollow medical needle 12, which typically is essentially no smaller than 18 gauge. Needle 12 is carried by hub 14, which also carries flexible wings 16, which may be of conventional design except for a reduced width. Particularly, wings 16 may have outer tips 18 that are spaced from each other by preferably no more than essentially 27 mm., which makes the wings relatively stubby and short, when compared with typical wings for winged needles of especially larger needles, like those needed for hemodialysis and blood collection, which are generally at least 34 mm. across in the similar tip-to-tip dimension. Despite this, the reduced width wings 16 can be readily grasped by a doctor or nurse to make venipuncture in a conventional manner, and which wings may be readily taped to the skin in an equally easy manner.

While at least one prior art butterfly needle set having a much thinner needle (27 gauge) has a tip-to-tip wing diameter of 28 mm., it appears that the prior art teaches that larger needles require wide wings for use, thus failing to appreciate the advantages of narrow wings as described herein.

Specifically, the spacing between wing outer tips 18 in a first embodiment of this invention may be about 26-27 mm.

Needle set 10 also comprises flexible set tubing 20, which is connected to hub 14 in a conventional manner (FIG. 3), where a first portion 61 of tubing 20 fits over and is retained on a tubular end of hub 14. Tubing 20 may terminate in a female luer lock connector 22 (FIG. 5) and may carry any other desired components, such as branch connection sites, branching tubes, drip chambers, injection sites, clamps, and the like.

It should further be noted that winged needle set 10 is shown in FIGS. 1 and 2 to be in "flipped" condition, when compared with the position of needle 12 in FIG. 3, where bevel 24 of needle 12 faces upwardly. In FIGS. 1 and 2, bevel 24 faces downwardly, indicating the flexibility of positioning provided by the guard of this invention.

Needle guard 30 is shown, particularly in FIG. 1, to comprise a flattened, relatively wide needle guard tube 32 which is free of wing receiving slots, and which defines a forward, open end 34. As illustrated particularly in FIG. 1, guard tube 32 may contain winged needle 12,14, 16 with the wings 16 being outwardly extending and substantially unbent as positioned within guard 30. Furthermore, guard 30 may comprise a fixed-dimension, open end or mouth 34 having a width of at least 20 mm. and a height of at least 5 mm. Specifically, the open mouth 34 may have a horizontal dimension of essentially at least 25-30 mm., for example about 28 mm., so as to be able to receive wings 16 having a transverse dimension of about 26-27 mm., as a specific embodiment.

Thus, needle 12 may be completely drawn into needle guard 30 and held therein as shown particularly in FIG. 5, so that the needle set 10 may be subsequently handled without risk of receiving an accidental needle stick.

Needle guard 30 also carries an anchor strip 36 which comprises a sheet of plastic material as shown, integrally attached to the top wall of needle guard tube 32 by a first flex line 38, which specifically may be a plastic living hinge of generally conventional construction. This permits vertical, transverse rotational movement of anchor strip 36 relative to guard tube 32. A second, living hinge flex line 40 is also defined in the anchor strip 32, spaced from first flex line 38, which also permits vertical rotational movement of an outer portion 42 of anchor strip 36. As shown, anchor strip 36 may define an upward curve at its outer end 44 to facilitate manual retention, in accordance with the teachings of Utterberg U.S. Pat. No. 5,951,529.

At forward, open end 34, bottom wall 46 of forward, open end 34 is shown to extend horizontally beyond the top wall 38 of needle guard 30, the forward end of which ends at first flex line 38. First and second flex lines 38, 40 are spaced apart at a distance of about the vertical spacing of open forward end 34, to permit anchor strip 36 to pivot about its flex lines 38, 40, to close end 34 in a manner particularly illustrated in FIG. 5. In this closed configuration, also shown in FIGS. 7 and 8, anchor strip 36 occupies an L-shaped configuration, with an outer portion 42 of anchor strip 36 lying against bottom wall 46. Thus, it can be seen that anchor strip 36 is easily rotated to close open front end 34 by the appropriate pivoting of flex lines 38, 40 to produce the L-shaped, closed configuration illustrated in FIGS. 5, 7 and 8. This can be facilitated by the presence of outwardly extending projection 50, which may be integrally molded with the rest of guard 30, preferably closed on all sides including ends 52 (FIG. 5), comprising part of anchor strip 36. Projection 50 facilitates the manual pivoting of the two flex lines 38, 40, which permits closing of the front end of the guard after needle 12 has been fully withdrawn into guard 30.

Guard 30 also carries a flow-blocking, tapered projection 54, which is proportioned with the outer shape of a male luer, to sealingly engage a female luer 22 of the winged needle set 10 that carries guard 30. The cutaway view of FIG. 3 shows how tapered projection 54 may be hollow, but has a flow blocking partition 56 which prevents it from functioning as a luer connector, but rather blocks flow and particularly blood spillage from a female luer connector that is carried upon it, in the manner illustrated by connector 22 in FIGS. 5 and 6. See U.S. Pat. No. 5,983,947. Thus, FIG. 5 shows how set 10, after use and containing residual blood in its interior, can be sealed at both ends by needle guard 30 to both provide protection against needle stick and also to prevent leakage of blood drops from the set.

As shown in FIG. 3, tube guardrails 58 are provided, two each on the top and bottom, and correspondingly positioned like the guardrail 58 specifically shown, to assist in centering of tube 20 as needle 12 is withdrawn into needle guard 30.

Needle guard 30 may be used by being initially carried on a rear portion of tube 20, with tube 20 extending through rear aperture 60 of guard 30, (FIG. 3) and extending out of open mouth 34. When it is desired to remove needle 12 from the tissue 62 of the patient, guard 30 may be pushed to slide it forwardly into the position shown in FIG. 4. Anchor strip 36 may overlie gauze pad 64, which, in turn, lies over the point 66 of needle entry into the tissue 62. The lower wall surface 46 of guard 30 may facilitate in passing under the needle wings 16, while anchor strip 36 passes over gauze 64. Then, the nurse's fingers 68 press downwardly on gauze 64 and anchor strip 36, as shown, and tube 20 may be gently pulled in the conventional manner to remove needle 12 from tissue, as described in Utterberg et al. U.S. Pat. No. 5,433,703. Upon such pulling, needle 12 is retracted, and wings 16 plus needle 12 pass into the interior of guard 30.

Figure 4:
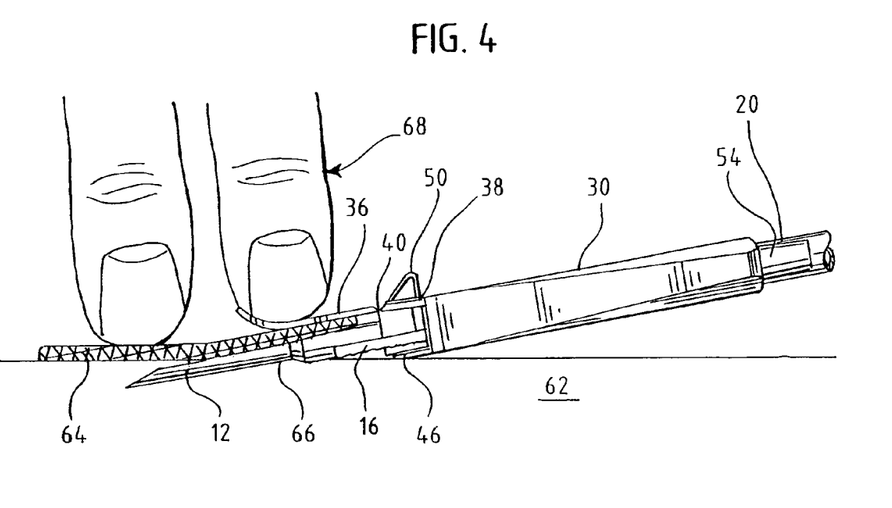
FIGS. 4 and 4a are elevational views of the needle set and guard of FIG. 1, in which the needle is shown in the process of being withdrawn from the tissue of a patient, sharing a gauze cover of differing thicknesses.
Figure 4A:
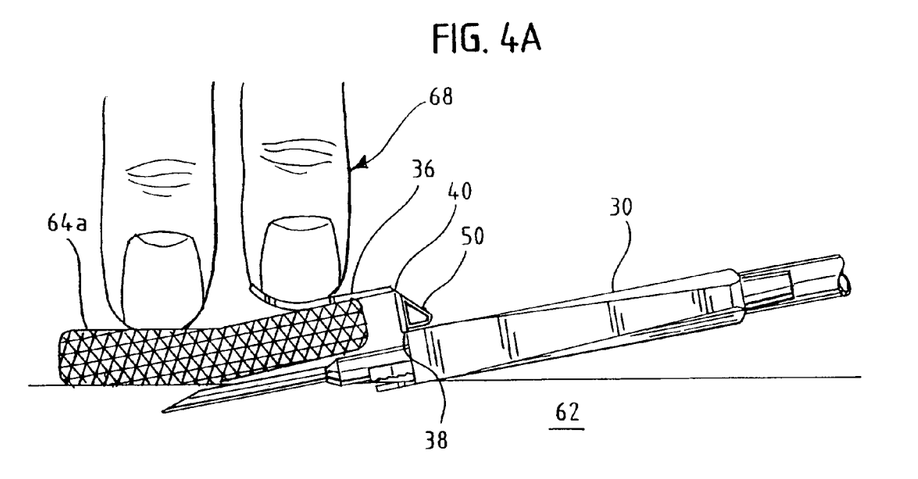

FIG. 4a shows how the process of FIG. 4 can also be performed with a thicker gauze pad 64a in similar manner with the thickness variation being accommodated for by the double hinges 38, 40 of anchor strip 36.

Figure 5:
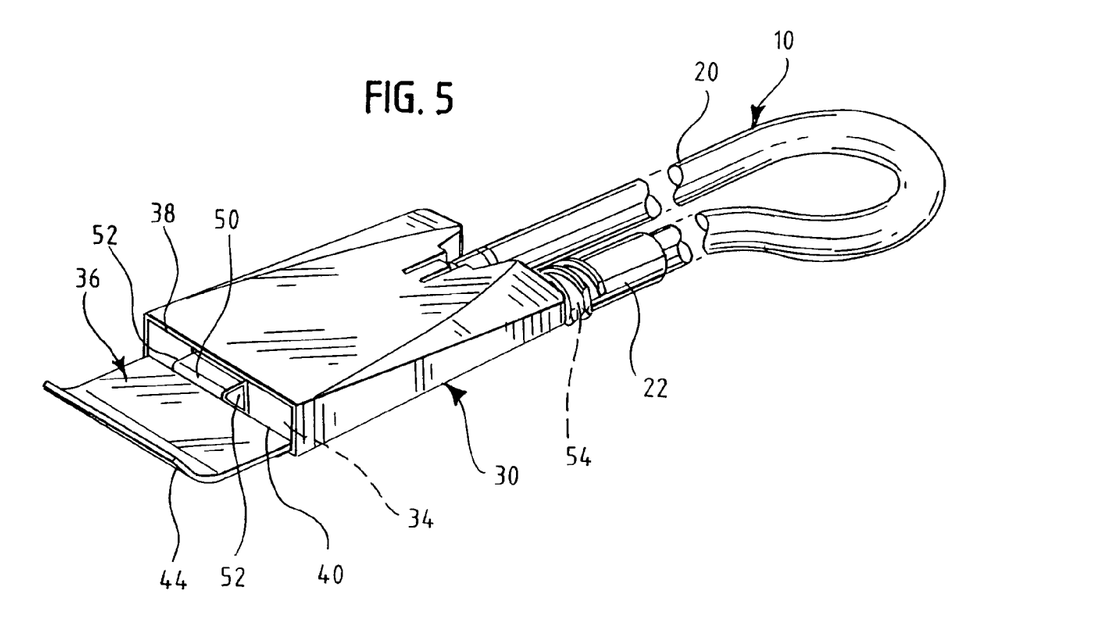
FIG. 5 is a perspective view of the winged needle set and the guard of the previous drawings in a final configuration, after the needle has been withdrawn from the patient, with both ends of the winged needle set being sealed by the guard.
Figure 6:
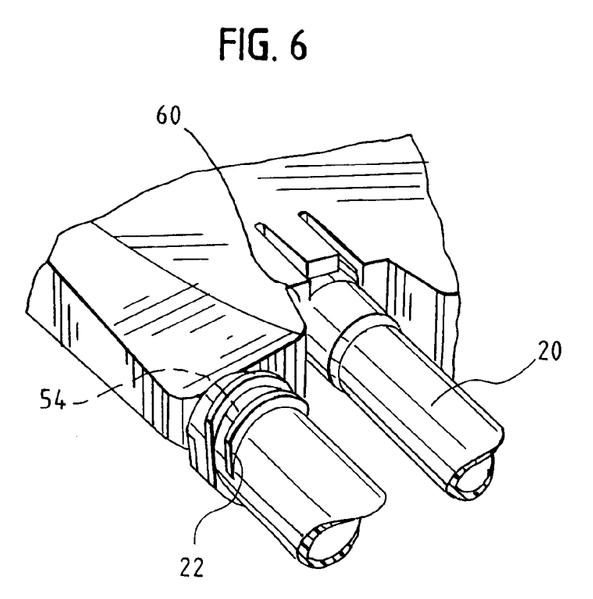
FIG. 6 is a detailed, enlarged rear perspective view of a portion of the guard and connected winged needle set.
Figure 7:
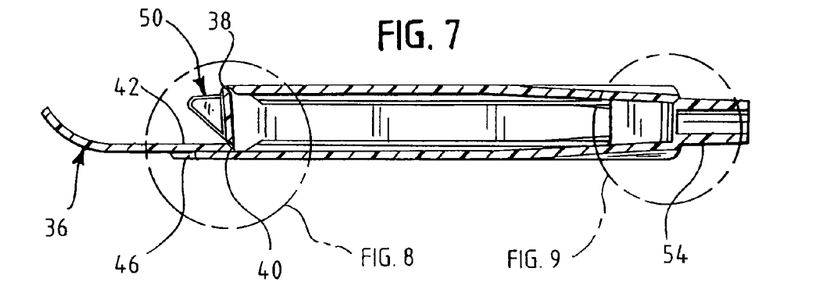
FIG. 7 is a longitudinal sectional view of the guard, without the winged needle set being shown, showing the guard in its closed, sealing configuration.
Figure 8:
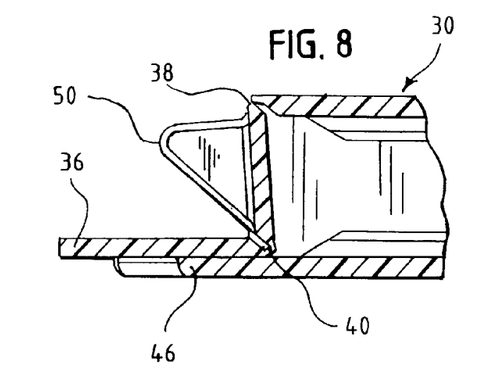
FIG. 8 is an enlarged, longitudinal sectional detail of the front end of the guard of FIG. 7.
Figure 9:
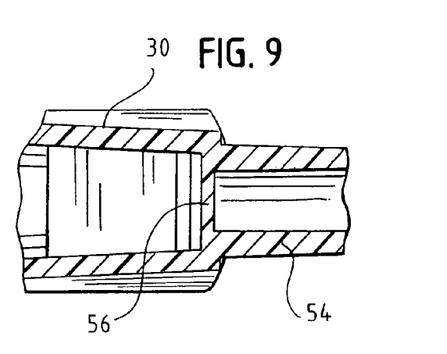
FIG. 9 is an enlarged, longitudinal sectional detail of the rear of the guard of FIG. 7.

Following this, one may manipulate projection 50 with the fingers to bend anchor strip into the L-shape as illustrated in FIGS. 5, 7, and 8, closing up open front end 34 to provide a front end seal, with the needle retracted and enclosed in guard 30. Then, as previously described, female luer lock connector 22 on the other end of set 10 may be attached to tapered projection 54, to completely seal the interior of set 10 while handlers of the used set are also protected against needle stick because the needle is completely enclosed.

Figure 3A:
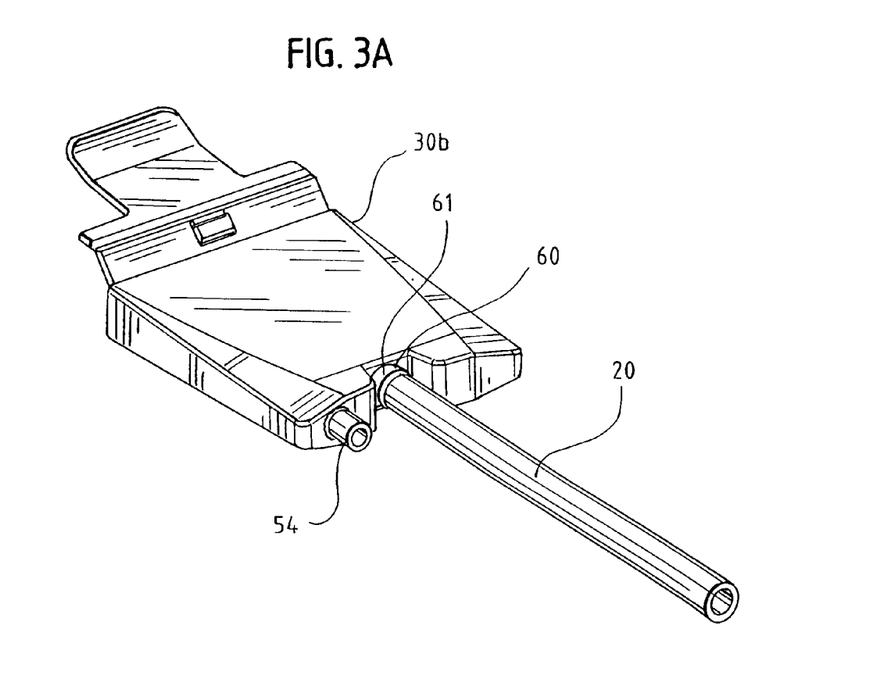
FIG. 3a is a rear perspective view of a guard similar to the guard of FIG. 3.

As shown in FIGS. 3 and 3a, rear aperture 60 may be sized to allow the flexible set tubing 20 to pass through it. Rear aperture 60 is defined by a ring edge that comprises an inner edge of a diameter to retentively engage the first portion 61 of set tubing 20 where the set tubing is slightly enlarged in diameter by its surrounding attachment to an end portion of hub 14, i.e., at tube section 61. The ring member at aperture 60 is thus typically slightly larger than the normal outer diameter of tubing 20. Tubing 20 slides easily through aperture 60. However, since the outer diameter of tubing 20 is slightly enlarged by its fitting around hub 14, when the needle is retracted as shown in FIG. 3a, ring edge 60 digs into the tubing section 61 to sealingly retain needle 12 in its retracted position, enclosed in the guard, while preventing leakage through aperture 60. FIG. 3 shows only a portion of ring 60, the remaining portion being furnished by the other half of guard 30. Pressure band 63 serves to help retain the connection between hub 14 and first tubing portion 61.

The detailed design and function of needle guard 30b in FIG. 3 is identical to that of guard 30, except as otherwise stated or shown.

Needle guard 30 may be used with any desired winged needle including conventional needles of enlarged wing transverse dimension, but preferably, a somewhat smaller, less bulky needle guard 30 may be provided for use with needle sets having wings of reduced transverse dimension as previously described herein.

Figure 10:
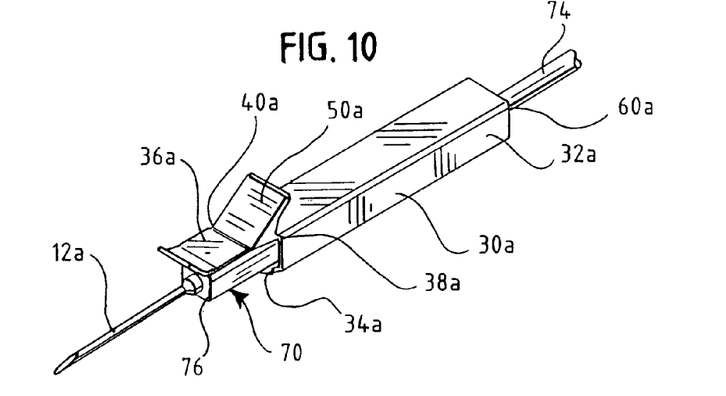
FIG. 10 is a perspective view showing a guard similar in construction to the guard of FIG. 1, but modified for use with a wingless needle set by means of a reduction in width.
Figure 11:
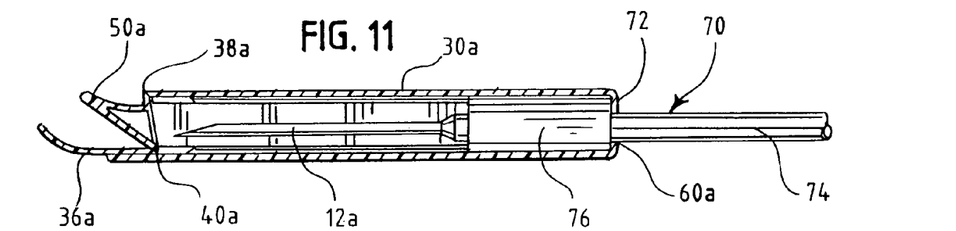
FIG. 11 is a longitudinal, sectional view of the guard of FIG. 10.

Referring to FIGS. 10 and 11, a conventional, wingless needle set 70 is shown, particularly comprising a Fenwal blood collection tube 74, needle 12a, and hub 76, are shown being guarded with another embodiment 30a of the needle guard of this invention. Needle guard 30a may be of essentially similar construction to that of needle guard 30 except for the reduced transverse dimension of guard 30a, since there are no wings in needle set 70 to be enclosed. As before, needle guard 30a comprises a needle guard tube 32a which is free of wing-receiving slots, and which defines a forward, open end 34a. Anchor strip 36a is provided, being of a structure and a function similar to that previously described, and having the first and second flex lines 38a, 40a for similar function as in the previous embodiment. Projection 50a may also be present, for manual folding of the flex lines 38a, 40a to close open mouth 34a, after needle 12a has been withdrawn into guard 30a, in a manner similar to the previous embodiment.

At the rear aperture 60a, a tube retention flange 72 that abuts hub 76 in FIG. 10 may be provided, having a diameter essentially equal to the outer diameter of tubing 74. Hub 76 abuts against flange 72 to limit retraction of hub 76 and needle 12a. A structure similar to tapered projection 54 is not included in this embodiment since needle set 70 is connected to a blood bag and, thus, no female luer connector is present requiring sealing.

The above has been offered for illustrative purposes only, and is not intended to limit the scope of the invention, which is as defined in the claims below.

The invention claimed is:

1. A winged needle set, which comprises:
a hollow medical needle which is essentially no smaller than 17 gauge carried by a hub, said hub also carrying wings projecting laterally outwardly from the hub in opposed directions, said wings having outer tips that are spaced from each other by essentially 20 to 30 mm, the hub being connected to flexible tubing; and
a self-supporting tubular, slot-free hollow needle guard carried on said tubing, said needle guard defining a forward, open end, said hollow guard being proportioned to receive and surround said winged needle with the wings generally projecting laterally outwardly, and the guard carrying a flow-blocking, tapered projection proportioned to sealingly engage a female luer of said winged needle set.

2. The winged needle set of claim 1 in which said outer tips are spaced by no more than essentially 25 mm.

3. The winged needle set of claim 1 in which said open end defines an aperture having a horizontal dimension of essentially at least 20 mm. and a vertical dimension of at least 3 mm.

4. The winged needle set of claim 1 in which said outer tips are spaced by no more than essentially 25 mm.

5. The winged needle set of claim 1 in which said needle guard defines a rear aperture through which said flexible tubing extends, said hub being connected with said flexible tubing with a first portion of the tubing being positioned outside and around a portion of said hub and defining an increased outer diameter, when compared with remaining portions of said flexible tubing, said rear aperture being sized to permit easy sliding of said remaining portions of said flexible tubing, while edges of said rear aperture bind against and form a seal with the first portion of the tubing when said first portion extends through said rear aperture.

6. A guard for a winged needle tube set having a hollow needle, a needle hub, and flexible set tubing attached to said hub, which comprises:
a needle guard tube which is free of wing-receiving slots and defining a forward, open end, said guard tube containing a winged needle of said set having outwardly extending, substantially unbent wings positioned within said guard, said guard comprising a substantially fixed—dimension open mouth having a width of at least 20 mm. and a height of at least 5 mm, and said guard carrying a flow-blocking, tapered projection proportioned to sealingly engage a female luer of said wind needle tube set.

7. The winged needle and flexible tubing of claim 6 in which said open mouth has a horizontal dimension of essentially at least 25 mm.

8. The guard of claim 6 in which said open mouth has a horizontal dimension of no more than essentially 30 mm.

9. The guard of claim 6 in which said needle guard tube has rear end with a rear aperture which is sized to allow said flexible set tubing to pass through it, and a ring defining said aperture, said ring edge having a diameter to retentively engage said set tubing where the set tubing is slightly enlarged in diameter by attachment to a portion of said hub within said set tubing, to retain said needle guard tube in a position that encloses the needle.

10. The guard of claim 6 in which said needle guard defines a rear aperture through which said flexible tubing extends, said hub being connected with said flexible tubing with a first portion of the tubing being positioned outside and around a portion of said hub and defining an increased outer diameter, when compared with remaining portions of said flexible tubing, said rear aperture being sized to permit easy sliding of said remaining portions of said flexible tubing, while edges of said rear aperture bind against and form a seal with the first portion of the tubing when said first portion extends through said rear aperture.

11. A guard for a needle tube set, which comprises:
a needle guard tube defining a forward, open end; an anchor strip attached to said forward end; a first flex line permitting transverse rotational movement of said anchor strip relative to said guard tube; and a second flex line defined in said anchor strip, spaced from said first flex line, permitting further rotational movement of an outer portion of said anchor strip, and a flow-blocking, tapered projection proportioned to sealingly engage a female luer of said winged needle rube set.

12. The guard of claim 11 in which said first flex line is connected to a top wall of said needle guard tube, and is substantially horizontal, to permit substantially vertical transverse rotational movement of said anchor strip.

13. The guard of claim 11 in which said forward, open end is partially defined by a bottom wall of said needle guard, which bottom extends horizontally beyond the top wall of said needle guard.

14. The guard of claim 13 in which said first and second flex lines are spaced apart at about the distance of the inner diameter of said open end, to permit said anchor strip to pivot to close said open end in which said anchor strip occupies an L-shaped configuration with the outer portion of the anchor strip lying against said bottom wall.

15. The guard of claim 14 in which said anchor strip defines an outwardly extending projection between said first and second flex lines.

16. The guard of claim 11 in which said needle guard defines a rear aperture through which said flexible tubing extends, said hub being connected with said flexible tubing with a first portion of the tubing being positioned outside and around a portion of said hub and defining an increased outer diameter, when compared with remaining portions of said flexible tubing, said rear aperture being sized to permit easy sliding of said remaining portions of said flexible tubing, while edges of said rear aperture bind against and form a seal with the first portion of the tubing when said first portion extends through said rear aperture.

17. The guard of claim 11 in which said needle guard tube has rear end with a rear aperture which is sized to allow said flexible set tubing to pass through it, and a ring edge defining said aperture, said ring edge having a diameter to retentively engage said set tubing where the set tubing is slightly enlarged in diameter by attachment to a portion of said hub within said set tubing, to retain said needle guard tube in a position that encloses the needle.

18. The guard of claim 11 in which said forward, open end is partially defined by a bottom wall of said needle guard, which bottom wall extends horizontally beyond the top wall of said needle guard.

19. The guard of claim 11 in which said first and second flex lines are spaced apart at about the distance of the inner diameter of said open end, to permit said anchor strip to pivot to close said open end in which such anchor strip occupies an L-shaped configuration with the outer portion of the anchor strip lying against said bottom wall.

20. The guard of claim 19 in which said anchor strip defines an outwardly extending projection between said first and second flex lines.

21. The guard of claim 11 which carries internal tube centering ribs.

22. The guard of claim 11, carried by a winged needle set.

23. A guard for a tubular set comprising flexible set tubing, which comprises:
a needle guard tube defining open ends so that the needle guard tube can slide on said set tubing, said needle guard tube carrying a flow-blocking, tapered projection proportioned to sealingly engage a female luer of said tubular set.

24. The guard of claim 23 which is free of needle wing-receiving slots.

25. The guard of claim 23 in which said guard defines a rear aperture through which said flexible tubing extends, said hub being connected with said flexible tubing with a first portion of the tubing being positioned outside and around a portion of said hub and defining an increased outer diameter, when compared with remaining portions of said flexible tubing, said rear aperture being sized to permit easy sliding of said remaining portions of said flexible tubing, while edges of said rear aperture bind against and form a seal with the first portion of the tubing when said first portion extends through said rear aperture.

* * * * *

UNITED STATES PATENT AND TRADEMARK OFFICE
CERTIFICATE OF CORRECTION

PATENT NO. : 7,591,804 B2
APPLICATION NO. : 11/407716
DATED : September 22, 2009
INVENTOR(S) : Utterberg et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 399 days.

Signed and Sealed this

Twenty-first Day of September, 2010

David J. Kappos
*Director of the United States Patent and Trademark Office*